US006482930B1

(12) United States Patent
Kwag et al.

(10) Patent No.: US 6,482,930 B1
(45) Date of Patent: Nov. 19, 2002

(54) MONOMERIC NEODYMIUM CARBOXYLATE AND ITS USE IN POLYMERIZATION OF CONJUGATED DIENE

(75) Inventors: Gwang Hoon Kwag, Taejon (KR); Seung Hwon Lee, Taejon (KR); Young Chan Jang, Taejon (KR); A Ju Kim, Taejon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 93 days.

(21) Appl. No.: 09/690,385

(22) Filed: Oct. 17, 2000

(30) Foreign Application Priority Data

Mar. 16, 2000 (KR) ......................................... 2000-13271

(51) Int. Cl.$^7$ .................................................. C07F 5/00
(52) U.S. Cl. ........................... 534/16; 534/15; 502/102; 502/170; 526/335; 526/340.2
(58) Field of Search ..................... 534/15, 16; 502/117, 502/118, 119, 128, 129, 131, 132, 102, 170; 526/335, 340.2

(56) References Cited

U.S. PATENT DOCUMENTS

| 5,360,898 A | 11/1994 | Jordaan et al. ................ 534/16 |
| 5,428,119 A | 6/1995 | Knauf et al. ................. 526/153 |
| 5,449,387 A | 9/1995 | Hawkins et al. .............. 44/364 |
| 5,877,109 A | * 3/1999 | Reichert et al. ............ 502/117 |

FOREIGN PATENT DOCUMENTS

| WO | 9736850 | 10/1997 | ..................... 51/41 |
| WO | 9839283 | 9/1998 | ..................... 51/41 |

* cited by examiner

Primary Examiner—David W. Wu
Assistant Examiner—R. Rabago
(74) Attorney, Agent, or Firm—Davidson, Davidson & Kappel, LLP

(57) ABSTRACT

The invention is related to a novel compound represented by $NdHA_4$ wherein A is a carboxylate, and to a diene polymerization catalyst using the novel compound. $NdHA_4$ has monomeric structure and does not contain water, bases and salts. $NdHA_4$ is mixed with a halogen compound and an organic metal compound to prepare a catalyst system. The catalyst system in the polymerization of 1,3-butadiene (BD) or isoprene produces high cis polydiene with a high activity (100 g BD/$4.0 \times 10^{-5}$ mole Nd) and without gel formation. The polydiene thus obtained is useful for tires and golf balls and as a polystyrene modifier.

2 Claims, No Drawings

MONOMERIC NEODYMIUM CARBOXYLATE AND ITS USE IN POLYMERIZATION OF CONJUGATED DIENE

TECHNICAL FIELD

The present invention generally relates to $NdHA_4$ (A=carboxylate), a novel monomeric neodymium carboxylate, and its use in the polymerization of a conjugated diene, and more particularly to $NdHA_4$ and a catalyst system comprising the same, halogen and organic metal compounds, which are usable in the polymerization of 1,3-butadiene or isoprene.

BACKGROUND OF THE INVENTION

The following conventional methods for preparing neodymium carboxylates have a common feature that the chemical formula of the neodymium carboxylaytes is $Nd(OOCR)_3$ wherein R represents an alkyl group.

As disclosed in WO 97/36850, WO 98/39283, British Patent No. 2,140,435, EUP Nos. 512,346 and 599,096, U.S. Pat. Nos. 5,428,119, 5,449,387 and 5,360,898, and Polymer (Vol 26, p147, 1985), $Nd(OOCR)_3$ was obtained by reacting an aqueous solution of lanthanide chloride, lanthanide nitrate or lanthanide oxide with an aqueous carboxylate solution, and by extraction followed with an organic solvent.

U.S. Pat. No. 5,220,045 discloses a method for preparing a neodymium carboxylate by reacting an aqueous neodymium nitrate solution with an organic acid dissolved in an organic solvent in the presence of ammonia or an organic base, and removing water by azeotropic distillation.

A method for preparing lanthanide carboxylates using the ligand exchange method is also described by Paul, R. C., Singh, G., and Ghota, J. S. (Indian J. Chem. Vol 11, p294, 1973).

However, the neodymium catalyst system thus obtained by the above method has an activity of no more than 7% (see. Porri. L. et al., Polymer Preprint, 1998, Spring p214) and adversely cause gel formation in the 1,3-butadiene polymerization.

This results from the fact that the neodymium carboxylate, $Nd(OOCR)_3$, has oligomeric or polymeric structures and contains lots of water, salts and bases which deteriorate the yield of in the polymerization and thereby lower the activity of the neodymium catalyst systems. In particular, the salts contained in the $Nd(OOCR)_3$, e.g., nitrates, chlorides and sulfates are difficult to eliminate. Furthermore, the solvents used in the synthesis of neodymium carboxylate, such as water, alcohols (e.g., methanol, ethanol), ethers (e.g., tetrahydrofuran, ethylether) or dimethylformamides will have coordinate with neodymium to lower the catalyst activity as well as agglomeration of the catalyst.

On the other hand, a conventional process for preparing high 1,4-cis polybutadiene with the conventional neodymium carboxylate is disclosed, for example, in EUP Nos. 11184 and 652240, and U.S. Pat. Nos. 4,260,707 and 5,017, 539, in which (1) neodymium carboxylate ($Nd(OOCR)_3$) (2) an alkylaluminium compound and (3) a Lewis acid are contacted in the presence of a non-polar solvent using a particular procedure to produce high 1,4-cis polybutadiene.

BRIEF SUMMARY OF THE INVENTION

In an attempt to develop a catalyst usable in the preparation of high cis polydiene and high catalyst activity without gel formation, the inventors have contrived a novel neodymium carboxylate compound $NdHA_4$ which has monomeric structure and does not contain water, bases and salts, and its use in the polymerization of diene with halogen and organic metal compounds.

Accordingly, it is an object of the present invention to provide a novel monomeric neodymium carboxylate, $NdHA_4$, of a high catalyst activity without gel formation when used in the preparation of polydiene.

It is another object of the present invention to provide a catalyst system comprising the novel monomeric neodymium carboxylate for polymerization of 1,3-budadiene or isoprene.

It is further another object of the present invention to provide a use of the polymerization catalyst in the preparation of polydiene having a very high 1,4-cis content (more than 96%).

To achieve the above objects of the present invention, there is provided a novel monomeric neodymium compound represented by $NdHA_4$, wherein A is a carboxylate containing 8 to 20 carbon atoms.

Furthermore, there is provided a diene polymerization catalyst including: (A) a novel monomeric neodymium compound represented by $NdHA_4$ according to claim 1; (B) a halogen compound; and (C) an organic metal compound.

DETAILED DESCRIPTION

The novel neodymium compound of the present invention is represented by $NdHA_4$ wherein A is a carboxylate containing 8 to 20 carbon atoms.

Examples of the carboxylate "A" in the formula may include neodecanoate (versatate), octoate, and naphthenate.

$NdHA_4$ can be prepared by ligand exchange between neodymium carboxylate or neodymium alkoxide and carboxylic acid in the presence of an organic solvent such as chlorobenzene. Preferably, examples of carboxylic acid may include versatic acid, 2-ethylhexanoic acid, naphthenic acid, and stearic acid.

$NdHA_4$ is activated in the mixture with a halogen or organic metal compound and used as a polymerization catalyst for polydiene.

$NdHA_4$ has a monomeric structure satisfying the minimum coordination number of 8 that provides high activity, prevents agglomeration of the neodymium compound and thus reduces gel formation of polydienes in polymerization.

Particularly, $NdHA_4$ is neutral without coordination with water, bases and salts so as to eliminate gel formation.

More specifically, a novel catalyst system for polymerization of 1,3-butadiene or isoprene is prepared by combining (A) $NdHA_4$, (B) halogen compound and (C) organic metal compound.

In regard to the second essential compound (B) used in the catalyst system, examples of the halogen compound may include, if not limited to, aluminum halogen compounds represented by $R^1{}_nAlX_{n-3}$ wherein $R^1$ is hydrogen or an alkyl or aryl group containing 1 to 10 carbon atoms, X is halogen, and n is an integer from 1 to 3; and inorganic or organic halogen compounds in which aluminum is completely substituted by boron, silicon, tin or titanium in the aluminum halogen compounds, wherein the organic halogen compounds are preferably alkyl halogen compounds containing 4 to 20 carbon atoms.

Preferably, examples of the organic metal compound as the third essential compound (C) of the catalyst system may include, if not limited to, alkyl aluminum compounds represented by $AlR^2{}_3$; alkyl magnesium compounds represented by $MgR^2{}_2$; alkyl zinc compounds represented by $ZnR^2{}_2$ and alkyl lithium compounds represented by $LiR^2$ wherein $R^2$ is hydrogen or an alkyl, cycloalkyl, aryl, arylaklyl or alkoxyl group containing 1 to 10 carbon atoms.

More specifically, examples of suitable organic metal compounds may include trimethyl aluminum, triethyl aluminum, tripropyl aluminum, tributyl aluminum, triisobutyl aluminum, trihexyl aluminum, diisobutyl aluminum hydride, dibutyl magnesium, diethyl magnesium, dibutyl zinc, diethyl zinc and n-butyl lithium.

$NdHA_4$ is mixed with a halogen compound and an organic metal compound, and then activated as a catalyst system fs' or the polymerization of diene in such a manner that diene is subjected to be polymerized in the presence of the catalyst system and a non-polar solvent at a temperature of 0 to 200° C. for 10 minutes to 5 hours.

In polymerization of 1,3-butadiene using $NdHA_4$, high cis polybutadiene thus obtained has a very high content (more than 95%) and high catalyst activity ($4.0 \times 10^{-5}$ mol Nd/100 g BD) without gel formation.

The catalyst system of the present invention can be prepared by mixing (A) $NdHA_4$, (B) halogen compound and (C) organic metal compound under a nitrogen atmosphere and aging the mixture in a non-polar solvent at a temperature of $-30$ to 60° C. for 5 minutes to 2 hours; or adding the three essential compounds in the order of (B), (C) and (A), (C), (B) and (A), or (A)-(B)-(C) to the reactor containing butadiene and a solvent.

It is desirable that the mole ratio of component (B) to component (A) is 1:1 to 1:20 and that the mole ratio of component (C) to component (A) is 1:10 to 1:200.

The suitable solvent used in polymerization is preferably a non-polar solvent not reactive with the components of the catalyst system. Examples of suitable solvent may include aliphatic hydrocarbons such as pentane, hexane, isopentane, heptane, octane and isooctane; cycloaliphatic hydrocarbons such as cyclopentane, methyl cyclopentane, cyclohexane, methyl cyclohexane and ethyl cyclohexane; and aromatic hydrocarbons such as benzene, toluene, ethylbenzene and xylene.

Optionally, diene may be added in the preparation of the novel catalyst system in order to maintain the catalyst activity, prevent precipitation and eventually control the property of the resulting polybutadiene. The amount of diene added is 2 to 10 times as large as that of the component (A) namely $NdHA_4$.

In the preparation of the catalyst system, the components are added to the reactor under a nitrogen atmosphere in the order of $NdHA_4$ solution, a halogen compound and an organic metal compound, but the addition order of the components is variable depending on the process.

In the presence of the novel catalyst system, 1,3-butadiene is polymerized in a non-polar solvent at a temperature of 0 to 200° C. for 10 minutes to 3 hours to produce polybutadiene having a very high content (more than 95%), a molecular weight of 100,000 to 2,000,000 and a Mooney viscosity of about 10 to 100.

Preferably, the ratio of 1,3-butadiene to non-polar solvent is 1:1 to 1:10.

On the other hand, a known reaction terminator, i.e., polyoxyethylene glycolphosphate and an antioxidant, i.e., 2,6-di-t-butyl para-cresol are further added in order to terminate the polymerization reaction of 1,3-butadiene. Finally, the resulting polybutadiene is obtained as a precipitate in methyl alcohol or ethyl alcohol, or under stream.

The following examples are intended to illustrate specific embodiments of the invention and are not intended to limit the scope of the invention.

EXAMPLE 1

Preparation of $NdH(neodecanoate)_4$

Chlorobezene (80 ml), neodymium acetate (3.2 g), neodecanoic acid (A, NEO ACIDS C10/Exxon Chemicals, 6.9 g, Mw. 173.7) were added to a 100 ml round bottom flask. The mixture was refluxed for 3 hours, the solvent was removed under vacuum (10 torr) with a rotary evaporator (at 50° C.), and then purified by gel chromatography (Bio-RAD, S-X12, toluene) to obtain blue-violet product (yield: 80%).

The product was analyzed for the structure by a mass spectroscopy (MALDI) and identified as $NdH(neodecanoate)_4$ ([M+1]=838.7).

EXAMPLE 2

Preparation of $NdH(C_8H_{15}COOH)_4$

Chlorobezene (80 ml), neodymium acetate (3.2 g) and 2-ethyl hexanoic acid ($C_8H_{15}COOH$, 5.8 g) were added to a 100 ml round bottom flask. The mixture was refluxed for 3 hours, and then the solvent was removed under vacuum (10 torr) with a rotary-evaporator (at 50° C.). $NdH(C_8H_{15}COOH)_4$ was isolated by gel chromatography (yield: 74%).

POLYMERIZATION EXAMPLE 1

Cyclohexane (150 ml), 1,3-butadiene (30 g), and diethyl aluminum chloride, diisobutyl aluminum hydride and triisobutyl aluminum were added to a 400 ml pressure glass reactor under a nitrogen atmosphere and aged at 40° C. for 30 minutes. To the mixture, there was added $NdH(neodecanoate)_4$ prepared in Example 1.

Here, $NdH(neodecanoate)_4$ was used as of 1.0% cyclohexane solution, and diethylaluminum chloride, diisobutylaluminum hydride and triisobutyl aluminum were used as of 15% $_n$-hexane solution. The concentration of NdH $(neodecanoate)_4$ Was $0.9 \times 10^{-4}$ mole per 100 g of the monomer. The mole ratios of the respective catalyst components are presented in Table 1.

After 2 hours, the reaction mixture was treated with 2,6-di-t-butyl para-cresol, polyoxyethylene phosphate and ethanol to obtain polybutadiene.

Polybutadiene was analyzed for Mooney viscosity, cis-content, molecular weight and molecular weight distribution. Solution viscosity of polybutadiene was determined in a 5.3% toluene solution with a Ubbelohde capillary viscometer. The results are presented in Table 1.

POLYMERIZATION EXAMPLES 2 and 3

$NdH(neodecanoate)_4$ obtained in Example 1 was used to prepare polybutadiene in the same procedure as described in Polymerization Example 1. The polybutadiene was analyzed for solution viscosity, Mooney viscosity, cis-content, molecular weight and molecular weight distribution, and the results are presented in Table 1.

TABLE 1

| | Polymerization Example No. | | |
|---|---|---|---|
| Div. | 1 | 2 | 3 |
| Nd Content ($10^{-4}$ mol/monomer 100 g) | 0.9 | 0.6 | 0.3 |
| Mole Ratio NdN/DEAC/Al(D/T) | 1/3/60(30/30) | 1/3/90(20/50) | 1/3/170(20/50) |
| S/M | 5 | 4 | 4 |
| SV | 226 | 230 | 297 |
| MV | 35.3 | 44.8 | 51.2 |
| Cis Content (%) | 97.2 | 96.3 | 97.0 |
| Mw ($10^5$) | 3.38 | 4.05 | 4.42 |
| MWD | 3.92 | 3.80 | 3.72 |

Note)
NdN: NdH(neodecanoate)$_4$
DEAC: Diethylaluminum chloride
D: Diisobutylaluminum hydride
T: Triisobutylaluminum

POLYMERIZATION EXAMPLES 4 to 6

NdH(C$_8$H$_{15}$COOH)$_4$ obtained in Example 2 was used to prepare polybutadiene in the same procedure as described in Polymerization Example 1. The polybutadiene was analyzed for solution viscosity, Mooney viscosity, cis-content, molecular weight and molecular weight distribution, and the results are presented in Table 2.

TABLE 2

| | Polmerization Example No. | | |
|---|---|---|---|
| Div. | 4 | 5 | 6 |
| Nd Content ($10^{-4}$ mol/monomer 100 g) | 1.1 | 0.7 | 0.4 |
| Mole Ratio NdN/DEAC/Al(D/T) | 1/3/70(20/50) | 1/3/60(10/70) | 1/3/140(40/100) |
| S/M | 5 | 5 | 5 |
| SV | 277 | 468 | 299 |
| MV | 40.1 | 65.8 | 54.6 |
| Cis Content (%) | 96.5 | 97.2 | 96.5 |
| Mw ($10^5$) | 4.13 | 5.20 | 5.07 |
| MWD | 3.90 | 4.20 | 4.23 |

Note)
Nd: NdH(octoate)$_4$
DEAC: Diethylaluminum chloride
D: Diisobutylaluminum hydride
T: Triisobutylaluminum As described above, NdHA$_4$ shows a high activity (100 g BD/4.0×10$^{-5}$ mole Nd) and produces high cis polybutadiene having more than 96% cis content without gel formation.

What is claimed is:

1. A monomeric neodymium compound represented by NdHA$_4$ wherein A is a carboxylate containing 8 to 20 carbon atoms.

2. The monomeric neodymium compound as claimed in claim 1, wherein the compound of NdHA$_4$ comprises at least one selected from the group consisting of NdH(neodecanoate)$_4$, NdH(octoate)$_4$ and NdH(naphthenate)$_4$.

* * * * *